United States Patent
DuBois

(10) Patent No.: US 7,560,512 B2
(45) Date of Patent: *Jul. 14, 2009

(54) ADHESIVE COMPOSITIONS COMPRISING MIXTURES OF BLOCK COPOLYMERS

(75) Inventor: Donn A. DuBois, Houston, TX (US)

(73) Assignee: Kraton Polymers U.S. LLC, Houston, TX (US)

(*) Notice: Subject to any disclaimer, the term of this patent is extended or adjusted under 35 U.S.C. 154(b) by 287 days.

This patent is subject to a terminal disclaimer.

(21) Appl. No.: 11/371,426

(22) Filed: Mar. 9, 2006

(65) Prior Publication Data

US 2006/0205878 A1  Sep. 14, 2006

Related U.S. Application Data

(63) Continuation-in-part of application No. 11/078,943, filed on Mar. 11, 2005, now abandoned.

(51) Int. Cl.
C08L 53/02 (2006.01)

(52) U.S. Cl. ............... 525/89; 524/474; 524/505

(58) Field of Classification Search ............... 525/89; 428/474, 505
See application file for complete search history.

(56) References Cited

U.S. PATENT DOCUMENTS

| | | | |
|---|---|---|---|
| 5,532,319 | A | 7/1996 | Asahara et al. |
| 5,583,182 | A | 12/1996 | Asahara et al. |
| 6,413,458 | B1 | 7/2002 | Pearce |
| 6,531,263 | B2 | 3/2003 | Knoll |
| 6,833,411 | B2 | 12/2004 | Fujiwara et al. |
| 7,001,956 | B2 | 2/2006 | Handlin, Jr. et al. |
| 2003/0232928 | A1 | 12/2003 | Atwood et al. |
| 2004/0116582 | A1 | 6/2004 | De Keyzer et al. |
| 2005/0137312 | A1 | 6/2005 | DuBois |
| 2006/0099373 | A1 | 5/2006 | Dupont et al. |
| 2006/0155062 | A1* | 7/2006 | De Keyzer ............... 525/88 |

FOREIGN PATENT DOCUMENTS

| | | |
|---|---|---|
| DE | 29 42 128 | 4/1981 |
| EP | 0 451 919 B1 | 9/1991 |
| EP | 0 532 831 A1 | 3/1993 |
| EP | 0 802 251 A1 | 10/1997 |
| EP | 1 597 331 B1 | 2/2004 |
| EP | 1 426 411 A1 | 6/2004 |
| EP | 1 493 790 A1 | 1/2005 |
| EP | 1 553 149 A1 | 7/2005 |
| EP | 1 566 423 A1 | 8/2005 |
| JP | 2004-131707 | 4/2004 |
| WO | 91/02039 | 2/1991 |
| WO | 00/14170 | 3/2000 |
| WO | 00/14170 A1 | 3/2000 |
| WO | 02/057386 | 7/2002 |
| WO | 2004/074394 A1 | 9/2004 |
| WO | 2004/097523 | 11/2004 |

OTHER PUBLICATIONS

K. Lee, et al. *Synthesis and Tensile Properties of Styrene-Butadiene-Isoprene Ternary Block Copolymer*; International Union of Pure Applied Chemistry; Jun. 30-Jul. 4, 2003, p. O48.

* cited by examiner

*Primary Examiner*—Jeffrey C Mullis
(74) *Attorney, Agent, or Firm*—Novak, Druce & Quigg LLP

(57) ABSTRACT

The present invention relates to adhesive compositions that comprise: i. at least one block copolymer (i)(a) of the formula A-I-A (1) or (A-I)$_n$X (2) and at least one block copolymer (i)(b) of the formula A-(I-B)-A (3) or [A-(I/B)]$_n$-X (4), wherein each A independently is a polymer block of an aromatic vinyl compound, I is a poly(isoprene) polymer block, (I/B) is a mixed random polymer block of isoprene and butadiene in a weight ratio I:B of from about 20:80 to about 80:20, n is an integer equal to or greater than 2 and X is the residue of a coupling agent, and wherein the weight ratio between said block copolymers (i)(a) and (i)(b) is such that the overall butadiene content in component (i) is less than 20 wt %, ii. a tackifying resin, and iii. optionally one or more plasticizers. Tapes, labels or bandages that are obtained by applying the adhesive compositions of the present invention to a carrier are also provided.

20 Claims, No Drawings

ADHESIVE COMPOSITIONS COMPRISING MIXTURES OF BLOCK COPOLYMERS

This application is a continuation in part of U.S. patent application Ser. No. 11/078,943, filed Mar. 11, 2005 now abandoned.

FIELD OF THE INVENTION

The present invention relates to adhesive compositions comprising mixtures of block copolymers. More particularly, the present invention relates to adhesive compositions comprising at least two block copolymers, each block copolymer having at least two poly(vinyl aromatic) blocks, and at least one poly(conjugated diene) block, one tackifying resin that is readily available and relatively inexpensive, and optionally one or more plasticizers. Even more specifically, the present invention relates to adhesive compositions comprising at least one block copolymer having two or more poly(vinyl aromatic) blocks and one poly(isoprene) block, at least one block copolymer having two or more poly (vinyl aromatic) blocks and one poly(isoprene/butadiene) block, a tackifying resin selected from C5 hydrocarbon resins and optionally, one or more plasticizers.

BACKGROUND OF THE INVENTION

Adhesive compositions based on styrenic block copolymers as thermoplastic elastomer components are well known in the art. These compositions are, for instance, used as pressure sensitive adhesives (PSA) for industrial tapes, packaging tapes and labels, and in multipurpose hot-melt adhesive compositions which may be used to bond or construct articles in the manufacture of disposable soft goods, such as diapers, feminine care articles, surgical drapes and the like.

Poly(styrene)-poly(isoprene)-poly(styrene) block copolymers (S-I-S) and poly(styrene)-poly(butadiene)-poly(styrene) block copolymers (S-B-S) are widely used in these adhesive compositions. Both classes of block copolymers give the adhesive compositions specific properties related to the respective inherent characteristics of these block copolymers. For example, the softness of S-I-S makes this polymer the material of choice for pressure sensitive applications in tapes and labels. Alternatively, the elevated cohesion of S-B-S makes this material attractive for construction adhesives for disposable soft goods.

When compounded into hot melt adhesives, S-I-S polymers degrade by a chain scission mechanism; molecular weight is reduced and the cohesive strength of the adhesive is lowered. S-B-S polymers, on the other hand, tend to degrade by further chemical cross-linking increasing the cohesive strength of the adhesive, but also increasing the elastic modulus, forming a too hard and non-tacky adhesive. The thermal decomposition of both S-I-S and S-B-S based adhesives can ruin the utility of the adhesive product. It would be an advantage to the hot melt adhesive industry if polymers with less tendency to either fall apart (scission) or cross-link would be developed. In EP-669350 and U.S. Pat. No. 5,583,182, adhesive compositions have been described wherein the styrenic block copolymer is a block copolymer of an S-B-I-S type, an $(S-B-I)_n$-X type or an $(S-I-B)_n$-X type, wherein S represents a polystyrene block, B represents a polybutadiene block and I represents an isoprene block. These copolymers with block copolymer midblocks "B-I" combine some of the characteristics of S-I-S and S-B-S type polymers. However, the process to make blocks of polydienes in the midblock is demanding, more complex and requires long polymerization times. It has also been demonstrated that because of the blocky structure in the midblock, their heat stability performance is still inadequate and that the hot-melt viscosity of formulated adhesives is too elevated for industrial applications compared to respectively S-I-S or S-B-S based formulations.

In WO 00/14170 an adhesive composition is described based on an elastomeric component comprising (I) an SIS block copolymer and (II) an SBS block copolymer, and on a tackifying component comprising (III) a first hydrocarbon resin compatible with said SIS block copolymer and (IV) a second hydrocarbon resin compatible with said SBS block copolymer. However, the necessity to use two block copolymers (SIS and SBS) as well as two hydrocarbon resins is not a cost effective approach for the manufacture of adhesive compositions, as it requires the adhesive manufacturers to invest deeply in expensive feeding and dosing systems on their extruders.

In DE-2942128 an adhesive composition is described based on 100 part of a non hydrogenated block copolymer A-B-A where A is polystyrene and B a block made of a mixture of Butadiene and Isoprene; from 25 to 300 part of a tackifying resin; from 5 to 200 part of a plasticizer, and some additional additives. Actually, the tackifying resin is a mixture of resins, as is illustrated in the example (50 parts of a glycerine rosin ester ("FLORAL" 85, a trademark) and 50 parts of a synthetic polyterpene resin ("WINGTACK" 95, a trademark)). This mixture appears to be required to be reasonably compatible with the base adhesive polymer.

From WO 02/057386A2 adhesive compositions are known, comprising:

i. one or more styrenic block copolymers of the general formula A-C-A (1) or $(A-C)_nX$ (2), wherein each A independently is a polymer block of an aromatic vinyl compound, a C is a mixed polymer block (B/I) of butadiene (B) and isoprene (I) in a weight ratio B:I in the range of from 30:70 to 70:30, and said polymer block C has a glass transition temperature (Tg) of at most −50 C. (determined according to ASTM E 1356-98) wherein n is an integer equal to or greater than 2 and X is the residue of a coupling agent, ii. a tackifying resin, having an aromaticity (in relative percentage of aromatic protons as determined by H-NMR) in the range of from 3 to 18% and preferably from 4 to 14%, iii. one or more plasticizers.

It will be appreciated that the aromatic modified tackifying resin was taught to be selected from a very specific group in combination with said block copolymers.

Mixtures of S-B-S and S-I-S type block copolymers as suggested in the art do not provide an acceptable alternative either.

Therefore, there is still a need for an adhesive composition in which (1) the adhesive properties are at least equal to those based on S-I-S block copolymers; (2) that shows an improved heat stability in comparison to a composition derived from S-I-S and/or S-B-S block copolymers; and (3) which can be formulated using a single hydrocarbon resin tackifier resin that is readily available and inexpensive.

SUMMARY OF THE INVENTION

As the result of extensive-research and experimentation, it has surprisingly been found that more cost effective adhesive compositions having adhesive properties which are at least equal to those based on SIS block copolymers can be achieved by combining an S-I-S or $(SI)_nX$ block copolymer with an S-(I/B)-S or $[S(I/B)]_nX$ block copolymer and a single tackifying resin. This combination results in lower costs of starting materials and manufacturing due to simpler processing, and lower cost non-aromatic resin.

Accordingly, an adhesive composition is provided that comprises:

i. at least one block copolymer (i)(a) of the formula A-I-A (1) or $(A-I)_n X$ (2) and at least one block copolymer (i)(b) of the formula A-(I/B)-A (3) or $[A-(I/B)]_n-X$ (4), wherein each A independently is a polymer block of an aromatic vinyl compound, I is a poly(isoprene) polymer block, (I/B) is a mixed random polymer block of isoprene and butadiene in a weight ratio I:B of from about 20:80 to about 80:20, n is equal to or greater than 2 and X is the residue of a coupling agent, and wherein the weight ratio between said block copolymers (i)(a) and (i)(b) is such that the overall butadiene content in component (i) is less than 20 wt %, ii. a C5 tackifying resin, and iii. optionally one or more plasticizers.

DETAILED DESCRIPTION OF THE INVENTION

Component (i)

As noted above, component (i) comprises:

at least one block copolymer (i)(a) having the formula:

A-I-A (1) or $(A-I)_n X$ (2);

wherein each A independently is a polymer block of an aromatic vinyl compound and each I is a poly(isoprene) polymer block, and at least one block copolymer (i)(b) having the formula:

A-(I/B)-A (3) or $[A-(I/B)]_n-X$ (4)

wherein each A independently is a polymer block of an aromatic vinyl compound and (I/B) is a mixed random polymer block of isoprene and butadiene in a weight ratio I:B of from about 20:80 to about 80:20.

Each n in the above formulas is independently equal to or greater than 2, preferably from 3 to 5, even more preferably from 3 to 4. Each X is the residue of a coupling agent to be specified hereinafter.

The block copolymer component (i)(a) can be selected from a great variety of block copolymers wherein the vinyl aromatic blocks are derived from styrene, alpha-methylstyrene, p-methylstyrene, o-methylstyrene, p-tert-butylstyrene, 2,4-dimethylstyrene, diphenylethylenes including stilbene, vinyl naphthalene, vinyltoluene (a mixture of meta- and para-isomers of methylstyrene), vinylxylene and mixtures thereof. Of these monomers, pure styrene or mixtures in which styrene is the main compound and minor amounts of one or more of the other hereinbefore mentioned comonomers are preferred. As used herein, the phrase "minor amounts" refers to amounts in the range of up to about 5 wt %, when present, typically present in an amount from about 1 to about 5 wt %. While the present invention is limited to those vinyl aromatic blocks which contain a "minor amount" of one or more comonomers, those of ordinary skill in the art will recognize that in certain instances, it may be desirable to use mixtures in which the one or more other hereinbefore mentioned comonomers are present in an amount greater than 5 wt %.

Each of the A blocks in formula (1) or (2) of component (i)(a) is independently a polymer block of an aromatic vinyl compound as defined hereinbefore and each I is a poly(isoprene) polymer block.

In said block copolymers of (i)(a) the A blocks represent a vinyl aromatic content which is the weight ratio of the vinyl aromatic block to conjugated diene block of the total block copolymer, in the range of from about 15 to about 45 wt %, preferably from about 15 to about 35 wt %, with the most preferred range being, from about 15 to about 25 wt %.

The block copolymers to be used as component (i)(a) each preferably contain 1,2-vinyl bonds and/or 3,4-vinyl bonds in a proportion of at most 15 wt %, based on the weight of the conjugated diene. While the present invention is limited to block copolymers of component (i)(a) that contain 1,2-vinyl bonds and/or 3,4-bonds in proportion of at most 15 wt %, those of ordinary skill in the art will recognize that 1,2-vinyl bonds and/or 3,4-vinyl bonds in a proportion of greater than 15 wt % are possible.

Preferably said A blocks in (i)(a) have a weight average molecular weight in the range of from about 5,000 to about 25,000, more preferably from about 7,000 to about 25,000. Preferred block copolymers to be applied as component (i)(a) show a weight average molecular weight (Mw) ranging from about 100,000 to about 500,000, more preferably from about 100,000 to about 250,000, and even more preferably from about 150,000 to about 250,000 as determined by High Performance Size Exclusion Chromatography (HPSEC) according to the method described in ASTM D-5296-97, said method incorporated herein by reference. Commercially available block copolymers which can be used as component (i)(a) of the present invention include, but are not limited to, KRATON® D-1126, and KRATON® D-1161, available from KRATON Polymers LLC, QUINTAC® 3620 and QUINTAC® 3450/3451, available from Zeon Chemicals and VECTOR® 4111, available from Dexco Polymers. The preferred commercially available selections are the block copolymers KRATON® D-1126 and KRATON® D-1161.

The block copolymer component (i)(b) can have the same or different A blocks as specified hereinbefore with regard to component (i)(a). However, the block copolymer component (i)(b) has (I/B) central blocks wherein the weight ratio of isoprene to butadiene is in the range of from about 20:80 to about 80:20, preferably from about 30:70 to about 70:30, even more preferably from about 40:60 to about 60:40, and still more preferably from about 45:55 to about 55:45, and wherein the isoprene/butadiene mixtures have randomly copolymerized, i.e. without any substantial homopolymer blocks, lengths pB and pI of more than 100 monomer units, and preferably not more than 20 monomer units. The mixed central polymer block (I/B) can optionally contain up to about 5 wt % of another copolymerizable comonomer such as styrene (based on the weight of the total block) but preferably said central block will be composed of mixtures of substantially pure isoprene and substantially pure butadiene.

Preferably said A blocks in (i)(b) also have a weight average molecular weight in the range of from about 5,000 to about 25,000, more preferably from about 7,000 to about 25,000. The block copolymers of component (i)(b) preferably have a weight average molecular weight (Mw, expressed in terms of poly(styrene)) ranging from about 100,000 to about 500,000, preferably from about 100,000 to about 250,000, even more preferably from about 150,000 to about 250,000, as determined by High Performance Size Exclusion Chromatography (HPSEC) according to the method described in ASTM D-5296-97.

The block copolymers to be used as component (i)(b) each preferably contain 1,2-vinyl bonds and/or 3,4-vinyl bonds in a proportion of at most 15 wt %, based on the weight of the conjugated diene. While the present invention is limited to block copolymers of component (i)(b) that contain 1,2-vinyl bonds and/or 3,4-bonds in proportion of at most 15 wt %, those of ordinary skill in the art will recognize that 1,2-vinyl bonds and/or 3,4-vinyl bonds in a proportion of greater than 15 wt % may also be possible.

In said block copolymers of (i)(b) the A blocks represent a vinyl aromatic content which is the weight ratio of the vinyl aromatic block to conjugated diene block of the total block copolymer, in the range of from about 15 to about 45 wt %, preferably from about 15 to about 35 wt %, with the most preferred range being from about 15 to about 25 wt %.

Polymers having mixed midblocks derived from isoprene and butadiene, are defined as having average homopolymer block lengths of less than 100 monomer units, preferably less than 50 monomer units, and more preferably less than 20 monomer units. Average homopolymer block length is determined by the method, based carbon-13 NMR, as described in detail in WO 02/057386, from page 12, line 14 to page 15, line 13, which is incorporated herein by reference.

The block copolymers according to the present invention can be made by e.g., coupling initially prepared living block copolymers, obtained by anionic polymerization, with a coupling agent, or by full sequential (co)polymerization of batches of vinyl aromatic monomer, conjugated diene and vinyl aromatic monomer respectively. It will be appreciated that mixtures of multiblock copolymers and preferably triblock copolymers, and diblocks originating from the starting living block copolymer to be coupled or by reinitiation during a full sequential polymerization process, can be obtained. The coupling agent, when used, can include, but are not limited to, tin coupling agents such as methyl tin trichloride, tin tetrachloride; halogenated silicon coupling agents such as silicon tetrachloride and silicon tetrabromide, alkoxysilanes such as tetramethoxysilane; and halogenated alkanes such as trichloroethane, trichloropropane and tribromopropane, divinyl aromatic compounds, halogenated aromatic compounds, epoxy compounds such as the diglycidyl ether of bisphenol-A and the like and other coupling agents such as benzoic esters, $CO_2$, 2-chloropropene and 1-chloro-1,3-butadiene. Silicon tetrachloride, silicon tetrabromide, tetramethoxysilane and other tetra(alkoxy)silanes are preferred.

Thus each coupled (or sequentially reinitiated) block copolymer may contain a complimentary diblock [A-I or A-(I/B)] where the ratio of block copolymer component to its complimentary diblock may range in weight ratio of from 100:0 to 30:70, preferably 90:10 to 40:60. It is also possible to blend in a diblock component prepared in a separate polymerization reaction. For example, a sequentially prepared A-I-A or A-(I/B)-A may be blended with a diblock [A-I or A-(I/B)] that was prepared in a separate polymerization reaction.

Accordingly, when prepared by coupling, the block copolymers used in the present invention have a Coupling Efficiency ("CE") of about 30 to 100 weight percent. Coupling Efficiency is defined as the proportion of polymer chain ends which were living, P-Li, at the time the coupling agent was added that are linked via the residue of the coupling agent at the completion of the coupling reaction. In practice, HPSEC data is used to calculate the coupling efficiency for a polymer product.

With regard to all of the embodiments of the present invention, the weight ratio between said block copolymers (i)(a) and (i)(b) is such that the overall butadiene content in component (i) is less than about 20 wt %. Preferably, the ratio is such that the overall butadiene content in component (i) is from greater than about 0 to about 18 wt %, more preferably from about 8 to about 16 wt % with the most preferred range being from about 10 to about 14 wt %.

Component (ii)

Suitable tackifying resins, which can be successfully used as the sole tackifying component in the adhesive composi-
tions of the present invention, show a differential scanning calorimetry (DSC) glass transition temperature Tg between 30 and 60° C. and a Ring and Ball softening point between 80 and 110° C. They can be selected from modified aliphatic hydrocarbon resins such as $C_5$ hydrocarbon resins. Suitable tackifying resins include, but are not limited to C5 resins that are not aromatic modified, such as for example, A-100 from Zeon Chemical, the ESCOREZ® 1000 series, especially ESCOREZ® 1202, from Exxon Mobil, and PICCOTAC® 1095 or PICCOTAC® 1098 from Eastman Chemical Company. The preferred tackifying resin to be used as the sole tackifying component (ii) is PICCOTAC® 1095, a modified aliphatic hydrocarbon resin, showing a Ring and Ball softening point of 95° C. The preferred solid tackifying resins will have a Ring and Ball softening point in the range of from 85 to 97° C.

Those of ordinary skill in the art will recognize that in some instances it might be possible to use aromatic modified resins to tackify the blends of the present invention provided that these resins are sufficiently low in aromaticity. Those of ordinary skill in the art also recognize that the more aromaticity the resin possesses will also allow greater overall butadiene content to be used in the PSA formulation. Accordingly, in some instances the degree of aromaticity will be low enough to allow such low aromatic resins to be used to achieve low cost products similar to those of the present invention.

The adhesive composition according to the present invention preferably comprises from about 50 to about 300 parts by weight, preferably from about 100 to about 200 parts by weight of tackifying resin per 100 parts by weight of block copolymer component (i) [components (i)(a) and (i)(b)]. In preferred adhesive compositions, the component (ii) occurs in a proportion of from about 30 to about 55 wt %, relative to the weight of the complete composition.

Component (iii)

The adhesive compositions of the present invention may contain one or more plasticizers. Suitable plasticizers include predominantly plasticizing oils that are paraffinic or naphthenic in character (carbon aromatic distribution $\leq 5\%$, preferably $\leq 2\%$, more preferably 0% as determined according to DIN 51378) and a glass transition temperature lower than $-55°$ C. as measured by Differential Scanning Calorimetry. Products such as these are commercially available from the Royal Dutch/Shell Group of companies, and include SHELLFLEX®, CATENEX™, EDELEX™ and ONDINA® oils. Other plasticizing oils that may be used include KAYDOL® oil from Witco, TUFFLO® oils from Arco or NYPLAST® from NYNAS. Still other plasticizers that are suitable for the present invention include compatible liquid tackifying resins such as REGALREZ® R-1018 from Eastman Chemical Company or WINGTACK® 10 from Goodyear Tire and Rubber Company.

Still other plasticizers may also be added, such as olefin oligomers; low molecular weight polymers ($\leq 30,000$ g/mol) such as liquid polybutene, liquid polyisoprene copolymers, liquid styrene/isoprene copolymers or liquid hydrogenated styrene/conjugated diene copolymers; vegetable oils and their derivatives; or paraffin and microcrystalline waxes.

The composition according to the present invention preferably comprises one or more plasticizers in a weight proportion of from about 5 to about 15 wt %, relative to the weight of the complete composition and of from about 10 to about 85 parts by weight of plasticizer per 100 parts by weight of block copolymer constituent (i) (components (i)(a) and (i)(b)). Also each block copolymer may be pre-blended with a small amount of plasticizer by the manufacturer of said copolymer.

Other Components (Non-Limitative)

Other rubber components may also be incorporated into the adhesive compositions according to the present invention. It is also known in the art that various other components can be added to modify the tack, the odor, and the color of the adhesives. Antioxidants and other stabilizing ingredients can also be added to protect the adhesive from degradation induced by heat, light and processing or during storage. When present, such ingredients are present in an amount from about 0 to about 10 parts by weight per 100 parts by weight of block copolymer component (i).

Several types of antioxidants can be used, either primary antioxidants such as hindered phenols or secondary antioxidants such as phosphite derivatives or blends thereof. Examples of commercially available antioxidants are IRGANOX® 565 from Ciba-Geigy (2.4-bis-(n-octylthio)-6-(4-hydroxy-3,5-di-tertiary-butyl anilino)-1,3,5-triazine), IRGANOX® 1010 from Ciba-Geigy (tetrakis-ethylene-(3,5-di-tertiary-butyl-4-hydroxy-hydrocinnamate) methane) IRGANOX® 1726 from Ciba-Geigy, IRGANOX® 1076 from Ciba-Geigy, ETHANOX® 330 from Albemare, IRGAFOS® 168 from Ciba-Geigy and POLYGARD® HR from Uniroyal (tris-(2,4-di-tertiary-butyl-phenyl)phosphite). Other antioxidants developed to protect the gelling of the polybutadiene segments can also be use, such as SUMILIZER® GS from Sumitomo (2[1-(2-hydroxy-3,5-di-ter-pentylphenyl)ethyl)]-4,6-di-tert-pentylphenylacrylate); SUMILIZER® T-PD from Sumitomo (pentaerythrythyltetrakis(3-dodecylthiopropionate)); or mixtures thereof.

Preparation of the Composition

No particular limitation is imposed on the preparation process of the adhesive compositions of the present invention. Therefore, there may be used any process such as a mechanically mixing process making use of rolls, a Banbury mixer or a Dalton kneader, a hot-melt process characterized in that heating and mixing are conducted by using a melting kettle equipped with a stirrer, like a high shear Z-blade mixer or a single- or twin-screw extruder, or a solvent process in which the compounding components are poured in a suitable solvent and stirred, thereby obtaining an intimate solution of the pressure sensitive adhesive composition.

Use of the Compositions

PSA compositions according to the present invention may be applied without using any solvent (e.g., hot-melt) or in the form of their solutions to a base material such as paper or a plastic film by means of a proper coater, thereby producing various kinds of pressure sensitive adhesive tapes for tapes or labels.

During label manufacture, a laminate of a face stock, pressure sensitive adhesive layer and a release liner are passed through an apparatus which converts the laminate into commercially useful labels and label stock. The process involves, among others, die-cutting and matrix stripping to leave labels on a release liner.

It will be appreciated that another aspect of the present invention is formed by tapes, labels or bandages obtained by application of the hereinbefore specified adhesive compositions of the present invention on a carrier.

The present invention will hereinafter be illustrated more specifically by the following examples, however without restricting the scope to these specific embodiments.

Test Methods

Standard peel, tack, cohesion and viscosity tests were carried out on these formulations as described in the Test method manual for Pressure Sensitive Tapes from the Pressure Sensitive Tape Council (PSTC), the standard FINAT test method for Pressure sensitive materials, the AFERA test methods for Pressure Sensitive Adhesive Tapes and the ASTM related methods. Different testing surfaces have been used in function of the application: chromed stainless steel plates (No. 304)("ss") as recommended by the FINAT and Kraft paper.

Rolling Ball Tack (RBT) is the distance, expressed in centimeters, a steel ball rolls on the adhesive film with a standard initial velocity (Pressure Sensitive Tape Council Method No. 6; ASTM D3121-73). Small numbers indicate aggressive tack.

Loop Tack (LT) was determined using Pressure Sensitive Tape Council Method No. 5 and FTM 9 loop tack method. High numbers LT indicate aggressive tack.

Peel Adhesion (PA) was determined by Pressure Sensitive Tape Council Method No. 1 and ASTM D3330-83. Large numbers indicate high strength when peeling a test tape from a steel substrate.

Holding Power (HP) is the time required to pull a standard area (2.5×1.3 cm) of tape from a standard test surface (steel=ss) under a standard load (1 kg, 2 or 5 kg), in shear at 2° (Pressure Sensitive Tape Council Method No. 7; ASTMD-3654-82). Long times indicate high adhesive strength. Results are expressed in hours (h) or minutes (min). The type of failure mode is expressed as adhesive failure (AF) or cohesive failure (CF). This test can be carried out at room temperature (about 23° C.) or at a more elevated temperature, depending on the test.

The SAFT (shear adhesion failure temperature) was measured by 2.5×2.5 cm Mylar to chromed ss plates with a 1 kg weight. The samples are placed in an oven and the temperature raised by 22° C./minute. SAFT measures the temperature at which the lap shear assembly fails.

Polystyrene content was determined by 1 H-NMR.

Ring and Ball softening point is a measure of the temperature at which a resin softens following the ASTM E-28 test method.

The compounds used in the tested adhesive compositions have been listed in Table 1

TABLE 1

| | |
|---|---|
| KRATON ® D 1126 | a linear poly(styrene)-poly(isoprene)-poly(styrene block copolymer with a 19% polystyrene content, a total molecular weight of about 210,000 g/mol and a coupling efficiency of 70% |
| KRATON ® D 1102 | a linear poly(styrene-poly(butadiene)-poly(styrene) with a polystyrene content of 28%, a total weight of 120,000 g/mol and a coupling efficiency of 84% |
| Block copolymer (i)(b) | a linear poly(styrene)-poly(isoprene/butadiene)-poly(styrene block copolymer having a isoprene/butadiene weight ratio of 60:40, a poly(styrene) content of 19%, a total molecular weight of about 180,000 g/mol and a coupling efficiency of 71% |
| SHELLFLEX ® 371 | a naphthenic oil from Shell Chemicals |
| IRGANOX ® 1010 | an antioxidant from Ciba-Geigy |
| PICCOTAC ® 1095 | a C5 aliphatic hydrocarbon resin with a softening point of 95° C., an aromaticity of 0% from Eastman Chemical Company. |

Adhesive compositions were prepared from 100 parts by weight of the block copolymer mixture (i), 110 parts by weight of tackifying resin (ii), 15 parts by weight of plasticizers oil (iii) and 3 parts by weight of an antioxidant.

The specific ingredients for each adhesive composition and the test results are listed in Table 2.

TABLE 2

SIBS/SIS Blend - function of BD content
SBS/SIS Blend

| FORMULATION<br>100 phr Polymer<br>110 phr Resin<br>15 phr Oil<br>3 phr Antioxidant<br>Composition, grams | D1126 Control | 10% wt BD | 12% wt BD | 16% wt BD | 20% wt BD | 30% wt BD | COMPARATIVE<br>SBS/SIS<br>Blend<br>11% wt BD |
|---|---|---|---|---|---|---|---|
| KRATON ® D1126 | 10 | 7.5 | 7 | 6 | 5 | 2.5 | 7 |
| Block Copolymer (i)(b) | 0 | 2.5 | 3 | 4 | 5 | 7.5 | 0 |
| KRATON ® D1102 | 0 | 0 | 0 | 0 | 0 | 0 | 3 |
| PICCOTAC ® 1095 | 11 | 11 | 11 | 11 | 11 | 11 | 11 |
| SHELLFLEX ® 371 | 1.5 | 1.5 | 1.5 | 1.5 | 1.5 | 1.5 | 1.5 |
| IRGANOX ® 1010 | 0.3 | 0.3 | 0.3 | 0.3 | 0.3 | 0.3 | 0.3 |
| Rolling Ball Tack (cm) | 4.9 | 5.2 | 5.2 | 13.9 | | | |
| Polyken Probe (kg) | 0.7 | 0.6 | 0.6 | 0.5 | 0.4 | 0.001 | 0.5 |
| Loop Tack (oz/in) | 108 | 119 | 118 | 102 | 103 | 17 | 134 |
| 180 Peel (pli) | 5.9 | 5.7 | 5.7 | 5.7 | 5.4 | 2.1 | 5.9 |
| 180 Peel Failure | Adhesive | Adhesive | Adhesive | Adhesive | Adhesive | Adhesive | Adhesive |
| HP Steel (min), 2 kg | >10,000 | >10,000 | >10,000 | >10,000 | >10,000 | >10,000 | >10,000 |
| HP Kraft (min), 2 kg | 8,386 | 5648 | 5125 | 3804 | 665 | 0 | 4113 |
| SAFT Mylar (° C.) 0.5 kg | 104 | 103 | 103 | 102 | 102 | 103 | 98 |

The data in Table 2 show that within a narrow and unanticipated range of total butadiene content, blends of SIS and SIBS polymers can be effectively tackified solely with an inexpensive C5 resin. Here, total polybutadiene content is defined as the polybutadiene content of the two block copolymer components (i)(a) and (i)(b).

Total polybutadiene content=(grams polybutadiene/
grams polyisoprene+grams polybutadiene)*100

Note that the polybutadiene content is not calculated basis the total formulation of polymers, resin, plasticizer and stabilizers.

In the range of approximately 0 to 18 wt % total polybutadiene content, adhesive properties are equivalent to the control formulation containing only the isoprene-based polymer KRATON® D-1126. Outside of the demonstrated range of total polybutadiene content the adhesive properties (especially RBT) become unacceptable and would require an aromatic modified resin to achieve comparable performance.

What is claimed is:

1. An adhesive composition comprising,
   i. at least one block copolymer (i)(a) of the formula A-I-A (1) or $(A-I)_nX$ (2), and at least one block copolymer (i)(b) of the formula A-(I/B)-A (3) or $[A-(I/B)]_n-X$ (4), wherein each A is independently a polymer block of an aromatic vinyl compound, each I is a poly(isoprene) polymer block, each (I/B) is a mixed random polymer block of isoprene and butadiene in a weight ratio of I:B of from 20:80 to 80:20, n is an integer equal to or greater than 2 and X is the residue of a coupling agent, and wherein the weight ratio between said block copolymers (i)(a) and (i)(b) is such that the overall butadiene content in component (i) is less than 20 wt %,
   ii. a single tackifying resin selected from modified aliphatic hydrocarbon resins that are not aromatic modified, and
   iii. one or more plasticizers.

2. The adhesive composition of claim 1, wherein the block copolymers (i)(a) and (i)(b) each have a poly(vinyl aromatic) content in the range of from 15 to 35 wt %.

3. The adhesive composition of claim 1, wherein the (I/B) weight ratio in the block copolymer (i)(b) is in the range of from 30:70 to 70:30.

4. The adhesive composition of claim 2, wherein the (I/B) weight ratio in the block copolymer (i)(b) is in the range of from 30:70 to 70:30.

5. The adhesive composition of claim 1, wherein the (I/B) weight ratio in the block copolymer (i)(b) is in the range of from 40:60 to 60:40.

6. The adhesive composition of claim 2, wherein the (I/B) weight ratio in the block copolymer (i)(b) is in the range of from 40:60 to 80:20.

7. The adhesive composition of claim 1, wherein the block copolymers (i)(a) and (i)(b) each have a weight average molecular weight in the range of from 100,000 to 500,000.

8. The adhesive composition of claim 6, wherein the block copolymers (i)(a) and (i)(b) each have a weight average molecular weight in the range of from 150,000 to 250,000.

9. The adhesive composition of claim 1, wherein the block copolymer (i)(a) comprises a multiblock copolymer according to formula (1) to (2) and a diblock copolymer A-I in a weight ratio in the range of from 100:0 to 30:70.

10. The adhesive composition of claim 9, wherein the block copolymer (i)(b) comprises a multiblock copolymer according to formula (2) to (4) and a diblock copolymer A-(I/B) in a weight ratio in the range of from 100:0 to 30:70.

11. The adhesive composition of claim 1, wherein the block copolymer (i)(b) comprises a multiblock copolymer according to formula (2) to (4) and a diblock copolymer A-(I/B) in a weight ratio in the range of from 100:0 to 30:70.

12. The adhesive composition of claim 1, wherein the tackifying resin shows a differential scanning calorimeter (DSC) glass transition temperature between 30 and 60° C.

13. The adhesive composition of claim 1, wherein the tackifying resin shows a softening point between 80 and 110° C.

14. The adhesive composition of claim 1, wherein the tackifying resin is a C5 hydrocarbon resin, showing a Ring and Ball softening point between 85 and 97° C.

15. The adhesive composition of claim 1, comprising from 50 to 300 parts by weight of resin per 100 parts by weight of block copolymer component (i).

16. The adhesive composition of claim 15, wherein the one or more plasticizers are present in an amount of from 10 to 85 parts by weight of plasticizer per 100 parts by weight of block copolymer component (i).

17. Tapes, labels or bandages that are obtained by applying an adhesive composition comprising,
  i. at least one block copolymer (i)(a) of the formula A-I-A (1) or $(A-I)_n X$ (2), and at least one block copolymer (i)(b) of the formula A-(I/B)-A (3) or $[A-(I/B)]_n$-X (4), wherein each A is independently a polymer block of an aromatic vinyl compound, each I is a poly(isoprene) polymer block, each (I/B) is a mixed random polymer block of isoprene and butadiene in a weight ratio of I:B of from 20:80 to 80:20, n is an integer equal to or greater than 2 and X is the residue of a coupling agent, and wherein the weight ratio between said block copolymers (i)(a) and (i)(b) is such that the overall butadiene content in component (i) is less than 20 wt %,
  ii. a single tackifying resin selected from modified aliphatic hydrocarbon resins that are not aromatic modified, and
  iii. one or more plasticizers, to a carrier.

18. The adhesive composition of claim 17, wherein the tackifying resin is a C5 hydrocarbon resin.

19. An adhesive composition comprising,
  i. at least one block copolymer (i)(a) of the formula A-I-A (1) or $(A-I)_n X$ (2), and at least one block copolymer (i)(b) of the formula A-(I/B)-A (3) or $[A-(I/B)]_n$-X (4), wherein each A is independently a polymer block of an aromatic vinyl compound, each I is a poly(isoprene) polymer block, each (I/B) is a mixed random polymer block of isoprene and butadiene in a weight ratio of I:B of from 20:80 to 80:20, n is an integer equal to or greater than 2 and X is the residue of a coupling agent, and wherein the weight ratio between said block copolymers (i)(a) and (i)(b) is such that the overall butadiene content in component (i) is less than 20 wt %,
  ii. a tackifying resin, iii. one or more plasticizers;
and wherein said composition excludes aromatic tackifying resins.

20. The adhesive composition of claim 17, wherein the tackifying resin is a C5 hydrocarbon resin.

* * * * *